US00PP30284P3

(12) United States Plant Patent
Miller

(10) Patent No.: US PP30,284 P3
(45) Date of Patent: Mar. 12, 2019

(54) ***LEUCADENDRON* PLANT NAMED 'REVERSE POLARITY'**

(50) Latin Name: *Leucadendron species*
Varietal Denomination: REVERSE POLARITY

(71) Applicant: Luen Miller, Soquel, CA (US)

(72) Inventor: Luen Miller, Soquel, CA (US)

( * ) Notice: Subject to any disclaimer, the term of this patent is extended or adjusted under 35 U.S.C. 154(b) by 0 days.

(21) Appl. No.: 15/731,609

(22) Filed: Jul. 8, 2017

(65) Prior Publication Data

US 2019/0014702 P1 Jan. 10, 2019

(51) Int. Cl.
*A01H 5/00* (2018.01)

(52) U.S. Cl.
USPC ..... Plt./226

(58) Field of Classification Search
USPC ..... Plt./263.1, 226
See application file for complete search history.

(56) References Cited

PUBLICATIONS https://pieceofeden.blogspot.com/2016/07/updates-on-recent-new-plants.html. Retrieved from the Interent on Jun. 25, 2018 (7 pages total).*

* cited by examiner

*Primary Examiner* — Susan McCormick Ewoldt
(74) *Attorney, Agent, or Firm* — Cassandra Bright

(57) ABSTRACT

A new and distinct *Leucadendron species* cultivar named 'REVERSE POLARITY' is disclosed, characterized by green mature foliage with a yellow central variegation and thin red margin. Floral bracts are variegated yellow-Green with Greyed-Purple 187B as a central streak. The new cultivar is a *Leucadendron*, typically suited for ornamental garden use, or as a cut flower.

4 Drawing Sheets

Latin name of the genus and species: *Leucadendron species.*

Variety denomination: 'REVERSE POLARITY'.

BACKGROUND OF THE INVENTION

The new variety originated as a chance discover by the inventor, Luen Miller. The variety was discovered as a naturally occurring branch mutation on a single plant of *Leucadendron species* 'Jester', unpatented. The new variety was discovered during June of 2011 at a commercial nursery in Royal Oaks, Calif. in a commercial planting of the parent variety.

After selecting and isolating the new cultivar, asexual reproduction of the new cultivar 'REVERSE POLARITY' was first performed at a commercial nursery in Royal Oaks, Calif. in July of 2013. Semi-softwood vegetative terminal cuttings were used for propagation. The inventor continued confidential, controlled evaluation and propagation of 'REVERSE POLARITY', to establish a stable clone. 'REVERSE POLARITY' has since produced three generations and has shown that the unique features of this cultivar are stable and reproduced true to type. Typical asexual reproduction of the new variety is by softwood vegetative cuttings.

SUMMARY OF THE INVENTION

The cultivar 'REVERSE POLARITY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'REVERSE POLARITY'. These characteristics in combination distinguish 'REVERSE POLARITY' as a new and distinct *Leucadendron* cultivar:

1. Mature foliage on mature branches is green with a yellow central variegation and very thin red margins.
2. The distinctive variegation pattern of the foliage is more intense in the floral bracts, which have a large Greyed-Purple center streak.
3. Suitability as a cut flower.

PARENTAL COMPARISON

Plants of the new cultivar 'REVERSE POLARITY' are similar to the parent in most horticultural characteristics. However, 'REVERSE POLARITY' differs in the following:

1. Variegation of the new variety is a central yellow streak, variegation of the parent variety is along the margin.
2. Floral bract variegation of the new variety is a darker color.
3. Plants of the new variety are much faster growing than plants of 'Jester'.
4. Plants of the new variety are more vigorous and disease resistant than plants of 'Jester'.

COMMERCIAL COMPARISON

Plants of the new cultivar 'REVERSE POLARITY' can be compared to the commercial variety *Leucadendron* 'Safari', unpatented. Plants of 'REVERSE POLARITY' are similar to plants of 'Safari' in most horticultural characteristics, however, plants of 'REVERSE POLARITY' differ in the following:

1. Foliage of the new variety is variegated, foliage of 'Safari' is solid green.
2. Floral bract color of the new variety is brighter, more intense than floral bract color of 'Safari'.

Plants of the new cultivar 'REVERSE POLARITY' can be compared to *Leucadendron* 'Rising Sun', unpatented. The new variety is similar in some horticultural characteristics. However, the plants of 'REVERSE POLARITY' differ in the following:

1. Foliage of 'Rising Sun' is solid green, the new variety has variegated foliage.
2. Flowering bract color of the new variety is variegated, flower bract color of 'Rising Sun' is solid.
3. Foliage of the new variety is larger than foliage of 'Rising Sun'.
4. Plants of the new variety produce larger stems than plants of 'Rising Sun'.
5. Plants of the new variety are more open and less dense than plants of 'Rising Sun'.

BRIEF DESCRIPTION OF THE PHOTOGRAPHS

The accompanying photographs were taken using conventional techniques and although colors may appear different from actual colors due to light reflectance it is as accurate as possible by conventional photographic techniques. Age of the plant photographed is approximately 2 years.

DETAILED BOTANICAL DESCRIPTION

Figure 1:
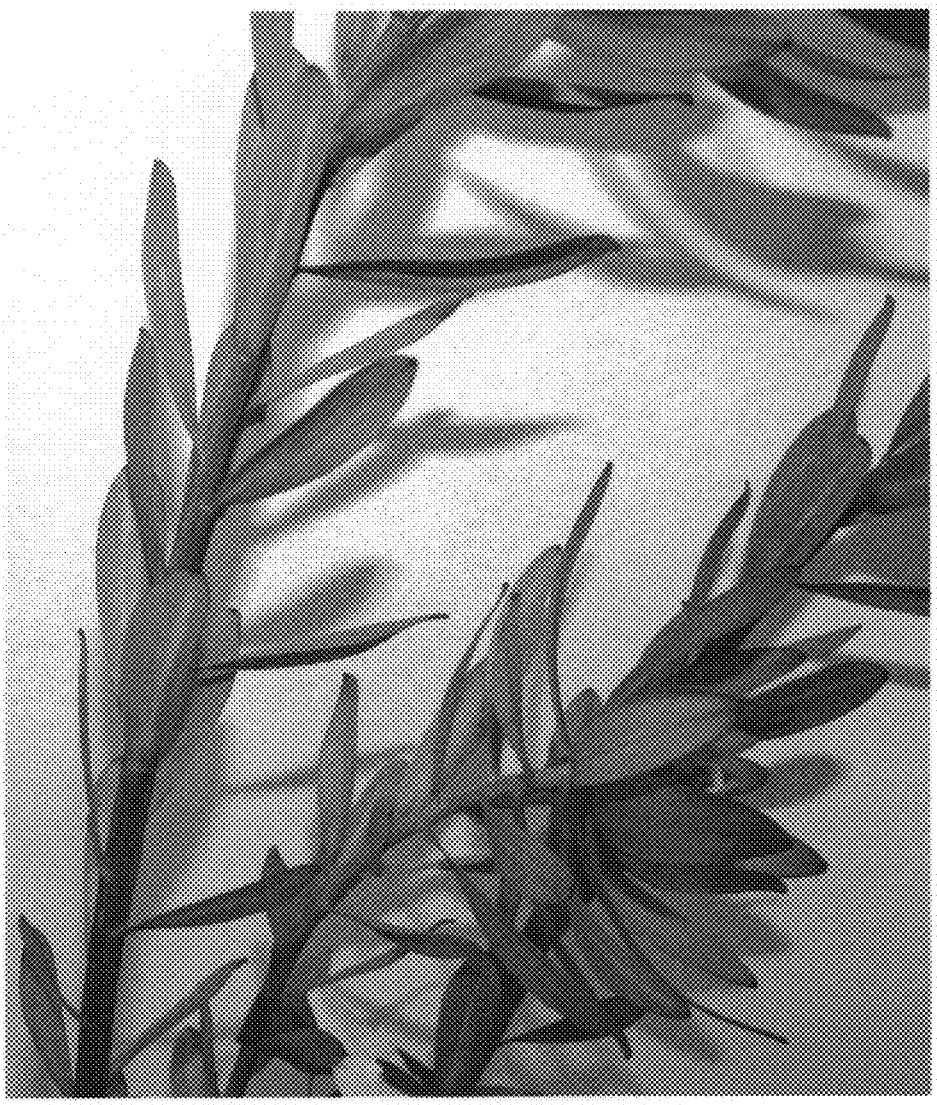
FIG. 1 illustrates a close up view of the stem and underside of the leaf, as well as the underside of a flower cone.
Figure 2:
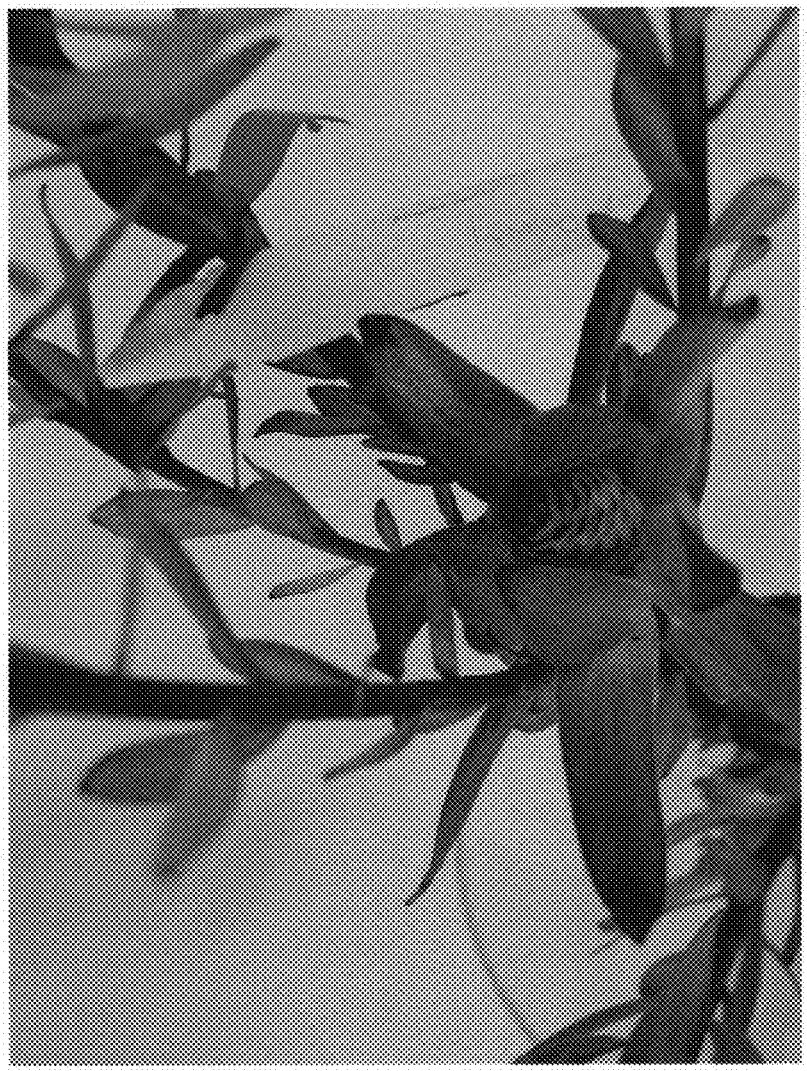
FIG. 2 illustrates a flowering cone from a top view.
Figure 3:
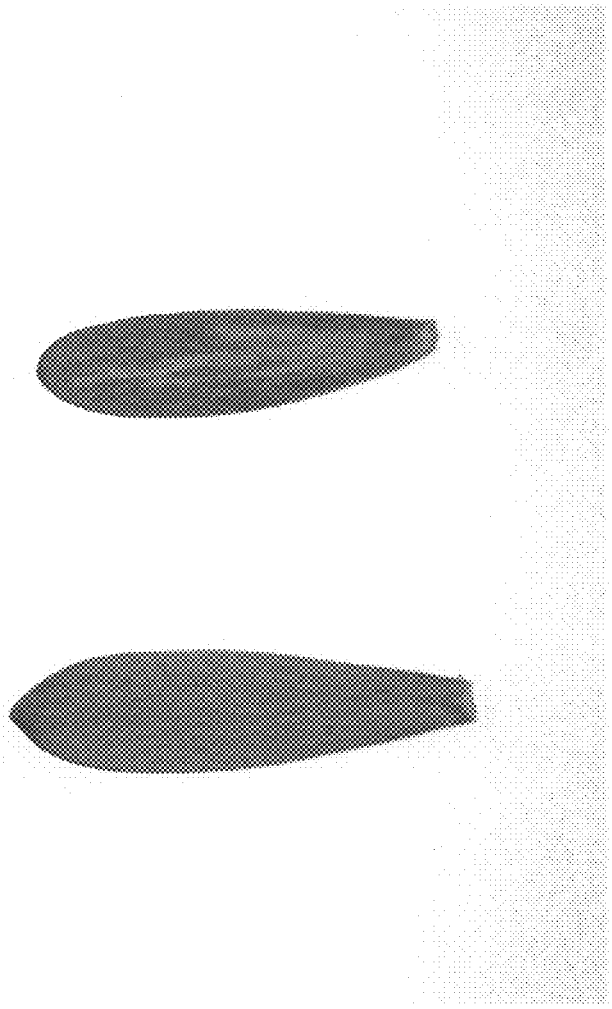
FIG. 3 illustrates upper and lower leaf surfaces of foliage grown on a plant in full sun conditions, with foliage fully exposed to sunlight. The leaf on the left is the underside, the leaf on the right is the upper surface.
Figure 4:
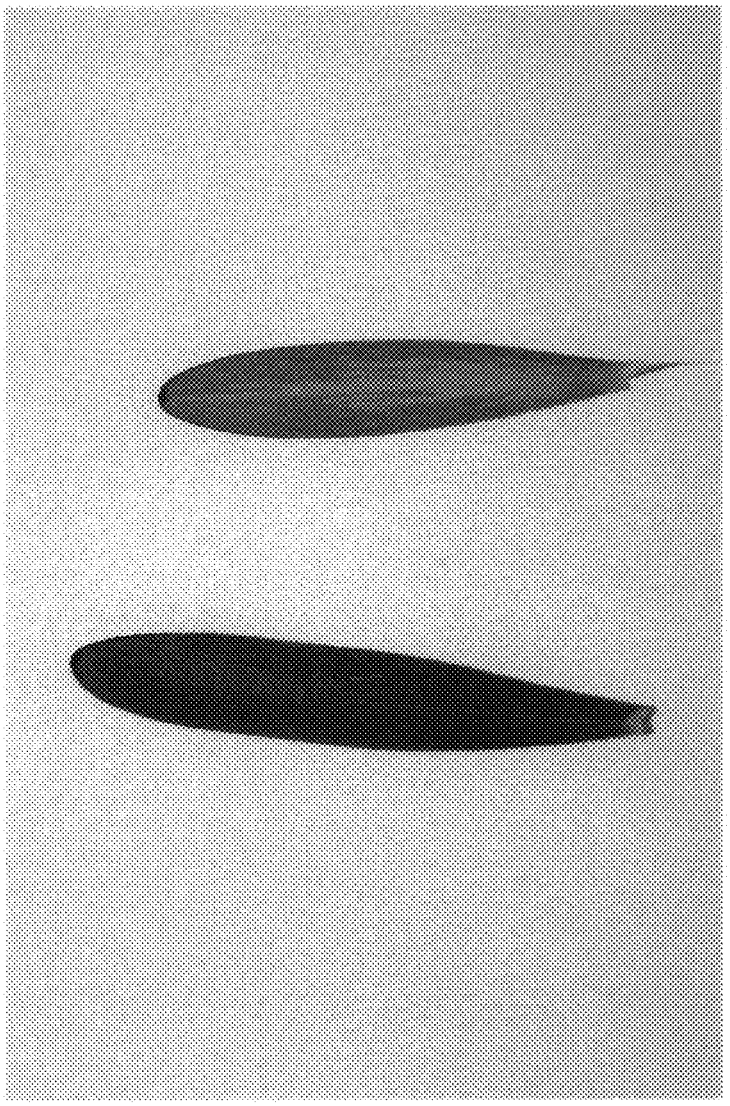
FIG. 4 illustrates foliage from the lower section of the plant, with very little sun exposure. The leaf on the left is the underside, the leaf on the right is the upper surface.

In the following description, color references are made to The Royal Horticultural Society Colour Chart, 2007, except where general terms of ordinary dictionary significance are used. The following observations and measurements describe 'REVERSE POLARITY' plants grown at a commercial nursery in Royal Oaks, Calif., under bright, unshaded conditions. Average day temperatures were approximately 8° C. to 26° C. and the average night temperature was approximately 3° C. to 18° C. No artificial light, photoperiodic treatments or chemical treatments were given to the plants. Measurements and numerical values represent averages of typical plant types.

Botanical classification: *Leucadendron species* 'REVERSE POLARITY'.

Age of the plant described: Approximately 2 years.

Container size of the plant described: 1 gallon commercial container.

PROPAGATION

Propagation method: Terminal cuttings, hardwood or semi-softwood.

Time to develop roots suitable for transplanting: About 6 to 8 weeks at an average temperature around 25° C.

Root description: Woody, not well branched, colored near Brown N199A and Grey-Brown 199A and 199B. Typically shallow rooted.

PLANT

Growth habit: Upright shrub.

Age of plant described: Approximately 2 years.

In a container or in the ground: 5 gallon container.

Height: 120 cm.

Plant spread: 25 cm.

Growth rate: Approximately 2 years to reach 120 cm in height.

Branching characteristics: Weak to moderate branching, a pinched plant produces 2 to 3 lateral branches on average.

Stem description:

- *Length*.—Approximately 17 cm before pinch.
- *Diameter*.—About 2.0 cm.
- *Texture*.—Glabrous, very slightly rough, no scales, bark or lenticels observed.
- *Strength*.—Very strong.
- *Color*.—Near RHS Greyed-Red 182C.

Lateral branches:

- *Length of primary lateral branches*.—Average range 30 to 60 cm.
- *Diameter of lateral branches*.—Approximately 0.7 cm.
- *Approximate quantity of lateral branches*.—5 to 10.
- *Branching arrangement*.—Whorled.
- *Texture*.—Glabrous.
- *Color*.—Lower section near Greyed-Purple 183D, upper section near Greyed-Purple 187A.

FOLIAGE

Leaf:

- *Arrangement*.—Spiral.
- *Quantity*.—Approximately 25 to 60, per main branch, including sub-branches.
- *Average length*.—5.5 cm.
- *Average width*.—Approximately 1.2 cm.
- *Shape of blade*.—Oblanceolate.
- *Apex*.—Acute.
- *Base*.—Truncate.
- *Margin*.—Entire.
- *Texture of top surface*.—Glabrous.
- *Texture of bottom surface*.—Glabrous.
- *Pubescence*.—None.
- *Aspect*.—Mainly flat, or with a very slight twist.
- *Color, full sun foliage*.—Young foliage upper side: Near RHS Yellow-Green 144A, about 1 to 2 mm center streaks near Yellow 3B. Young foliage under side: Near RHS Yellow-Green 144A, about 1 to 2 mm center streaks near Yellow 3B. Mature foliage upper side: Near RHS Green 138A. Thick center streaks 3B. Base often flushed Red 53B and 53C, colors occurring individually. Thin margin near 53B. Mature foliage under side: Near RHS Green 138A. Thick center streaks 3B. Base often slight flushed Red 53D. Thin margin near 53B.

*Venation*.—Type: Pinnate. Venation color upper side: Indistinguishable from foliage coloration. Venation color under side: Indistinguishable from foliage coloration.

*Petiole*.—No present, sessile.

FLOWER

Natural flowering season: Year round in temperate California conditions.

Begins flowering after how many years/months: About 1 year.

Inflorescence type and habit: Female only flowers. Minute flowers occurring in gently spiraling rows on conical spikes. Flowers tubular structure of fused petals, outwardly facing. Flower self-cleaning, persisting approximately 8 weeks on the spike.

Quantity of flowers per inflorescence: 56 to 64, occurring in 7 or 8 rows of 8 flowers.

Inflorescence size:

*Diameter*.—Approximately 1.8 cm.

*Height*.—Approximately 2.5 cm.

Individual flowers:

*Size*.—

*Diameter*.—Approximately 1 mm.

*Length*.—Approximately 1.5 mm.

*Shape*.—Tubular.

Petals:

*Petal arrangement*.—Fused, tubular.

*Size*.—Length: 1 mm. Width: Less than 1 mm.

*Margin*.—Entire.

*Apex*.—Rounded.

*Base*.—Fused.

*Petal quantity*.—Indistinguishable, single, minute structure.

*Texture*.—Glabrous.

Color:

*Petals*.—When opening: Inner surface: Near RHS Greyed-Purple N186A. Outer surface: Near RHS Greyed-Purple N186A. Fully opened: Inner surface: Near RHS Greyed-Purple N18&A. Outer surface: Near RHS Greyed-Purple N187A.

Bud:

*Shape*.—Ovate.

*Length*.—Approximately 0.5 mm.

*Diameter*.—Approximately 0.4 mm.

*Color*.—Near RHS Greyed-Purple N186A.

Fragrance: None.

Involucral bracts:

*Number*.—Average range 12 to 16.

*Length*.—Approximately 0.7 cm.

*Width*.—Approximately 0.5 cm.

*Shape*.—Deltate.

*Texture*.—Glabrous.

*Apex shape*.—Acute.

*Margin*.—Entire.

*Color*.—Near RHS Greyed-Purple 183A.

Floral bracts:

Description: Leaf like, occurring just below inflorescence.

*Quantity*.—Average range 8 to 10.

*Arrangement*.—Spiral.

*Average length*.—6.8 to 7.5 cm.

*Average width*.—Lower 1.7 cm, inner 2.5 cm.

*Shape of blade*.—Oblanceolate.

*Apex*.—Acute.

*Base*.—Truncate.

*Margin*.—Entire.

*Texture of top surface*.—Glabrous.

*Texture of bottom surface*.—Glabrous.

*Pubescence*.—None.

*Aspect*.—Strong upward cupping, very light undulation or twist.

*Color*.—Upper surface: Center near RHS Yellow-Green N144A, heavily flushed Greyed-Purple 187B. Margin near 187B. Under surface: Center near RHS Yellow-Green N144A, heavily flushed Greyed-Purple 187B. Margin near 187B.

Peduncle: Beginning from the lowermost floral bract to the uppermost leaf.

*Length*.—Approximately 2 cm.

*Diameter*.—Approximately 0.4 cm.

*Texture*.—Glabrous.

*Color*.—Near Red 53A.

REPRODUCTIVE ORGANS

Minute flowers with compressed productive organs. Reproductive organs not visible under a dissecting microscope.

OTHER CHARACTERISTICS

Seeds and fruits: No seeds/fruits observed.

Disease/pest resistance: Observed improved resistance to foliar diseases of *Leucadendron*. The assumed foliar diseases are fungal, presumably *Dreschlera, Colletrichium* or *Elsinoe*. No other resistance nor susceptibility to normal pests and diseases of *Leucadendron* has been observed.

Temperature tolerance: Tolerates low temperatures to approximately −9° C. Good high temperature tolerance, observed to at least 40° C.

What is claimed is:

1. A new and distinct cultivar of *Leucadendron* plant named 'REVERSE POLARITY' as herein illustrated and described.

* * * * *